US006942773B1

(12) United States Patent
Olivares et al.

(10) Patent No.: US 6,942,773 B1
(45) Date of Patent: Sep. 13, 2005

(54) PARTICLE SIZER AND DNA SEQUENCER

(75) Inventors: José A. Olivares, Los Alamos, NM (US); Peter C. Stark, Los Alamos, NM (US)

(73) Assignee: The Regents of the University of California, Oakland, CA (US)

(*) Notice: Subject to any disclaimer, the term of this patent is extended or adjusted under 35 U.S.C. 154(b) by 544 days.

(21) Appl. No.: 09/771,277

(22) Filed: Jan. 26, 2001

(51) Int. Cl.[7] .................. G01N 27/447; G01N 27/453
(52) U.S. Cl. ............................... 204/452; 204/603
(58) Field of Search ............................. 204/452, 603

(56) References Cited

U.S. PATENT DOCUMENTS

| | | | |
|---|---|---|---|
| 4,964,961 A | 10/1990 | Brautigam et al. | 204/182.8 |
| 5,151,165 A | 9/1992 | Huynh | 204/299 R |
| 5,284,559 A | 2/1994 | Lim et al. | 204/182.8 |
| 5,338,427 A | * 8/1994 | Shartle et al. | 204/604 |
| 5,395,502 A | 3/1995 | Pawliszyn | |
| 5,627,643 A | 5/1997 | Birnbaum et al. | |
| 5,694,215 A | 12/1997 | Carver | |
| 5,699,157 A | 12/1997 | Parce | |
| 6,042,708 A | 3/2000 | Nakanishi et al. | |

FOREIGN PATENT DOCUMENTS

| | | |
|---|---|---|
| JP | 10-19846 | 1/1998 |
| WO | WO 99/39192 | 8/1999 |
| WO | WO 00/04371 | 1/2000 |

OTHER PUBLICATIONS

Beale & Sudmeier, "Spatial–Scanning Laser Fluorescene Detector for Capillary Electrophoresis" Analytical Chemistry vol. 67, No. 18, Sep. 15, 1995 pp. 3367–3371.*

(Continued)

*Primary Examiner*—Alex Noguerola
(74) *Attorney, Agent, or Firm*—Madson & Metcalf (57) ABSTRACT

An electrophoretic device separates and detects particles such as DNA fragments, proteins, and the like. The device has a capillary which is coated with a coating with a low refractive index such as Teflon® AF. A sample of particles is fluorescently labeled and injected into the capillary. The capillary is filled with an electrolyte buffer solution. An electrical field is applied across the capillary causing the particles to migrate from a first end of the capillary to a second end of the capillary. A detector light beam is then scanned along the length of the capillary to detect the location of the separated particles. The device is amenable to a high throughput system by providing additional capillaries. The device can also be used to determine the actual size of the particles and for DNA sequencing.

46 Claims, 5 Drawing Sheets

OTHER PUBLICATIONS

Suhyeon Kim et al. "Postelectrophoresis Capillary Scanning Method for DNA Sequencing" Analytical Chemistry, vol., 68, No. 5 Mar. 1, 1996 pp. 936–939.*

Jianzhong Li et al, "Transversely Illuminated Liquid Core Waveguide Based Fluorescence Detection. Fluorometric Flow Injection Determination of Aqueous Ammonium/Ammonia" Talanta, vol. 50 (1999) pp. 617–623.*

"Laser–Induced Fluorescence Detection by Liquid Core Waveguiding Applied to DNA Sequencing by Capillary Electrophoresis", A. Hanning et al., *Analytical Chemistry*, vol. 72, No. 15, Aug. 1, 2000, pp. 3423–3430.

"Small–Volume Raman Spectroscopy with a Liquid Core Waveguide", M. Holz et al., *Analytical Chemistry*, vol. 71, No. 14, Jul. 15, 1999, pp. 2934–2938.

"Transversely Illuminated Liquid Core Waveguide Based Fluorescence Detection Fluorometric Flow Injection Determination of Aqueous Ammonium/Ammonia", J. Li et al., *Talanta 50*, 1999, pp. 617–623.

"Chemiluminescence Detection with a Liquid Core Waveguide Determination of Ammonium with Electrogenerated Hypochlorite Based on the Luminol–Hypochlorite Reaction", J. Li et al., *Analytical Chimica ACTA* 398, 1999, pp. 33–39.

"Luminescence Detection with a Liquid Core Waveguide", P. Dasgupta et al., *Analytical Chemistry*, vol. 71, No. 7, Apr. 1999, pp. 1400–1407.

"Multi–Capillary Optical Waveguides for DNA Sequencing", M. Quesada et al., *Electrophoresis*, 1998, pp. 1415–1427.

"Time and Wavelength–Resolved Fluorescence Detection for Capillary Zone Electrophoresis with Axial Excitation", A. Fultz et al., *Microchemical Journal*, 57, 1997, pp. 231–244.

"An Electro–Osmotic Flow System with Integrated Planar Optical Waveguide Sensing", J. Leeney et al., *Sensors and Actuators B Chemical*, 1997, pp. 212–217.

"Real–Time Fluorescence Imaging of Isotachophoretic Preconcentration for Capillary Electrophoresis", J. Johannsson et al., *Analytical Chemistry*, vol. 68, No. 17, Sep. 1, 1996, pp. 2766–2770.

"Postelectrophoresis Capillary Scanning Method for DNA Sequencing", S. Kim et al., *Analytical Chemistry*, vol. 68, No. 5, Mar. 1, 1996, pp. 936–939.

"Kinetics of the Interaction Between DNA and the Type IC Restriction Enzyme EcoR123II", J. Ramsden et al., *Biochemistry*, vol. 35, 1996, pp. 3746–3753.

"Spacial–Scanning Laser Fluorescence Detection for Capillary Electrophoresis", S. Beale et al., *Analytical Chemistry*, vol. 67, No. 18, Sep. 15, 1995, pp. 3367–3371.

"Real–Time Fluorescence Imaging of Capillary Electrophoresis", S. Nilsson et al., *J. Cap. Elec.*, 1995, pp. 46–52.

"Imaging Detection Methods for Capillary Isoelectric Focusing", J. Wu et al., *American Laboratory*, Oct. 1994, pp. 48–52.

* cited by examiner

PARTICLE SIZER AND DNA SEQUENCER

GOVERNMENT RIGHTS STATEMENT

This invention was made with Government support under Contract No. W-7405-ENG-36 awarded by the United States Department of Energy to The Regents of the University of California. The Government has certain rights in the invention.

FIELD OF THE INVENTION

The present invention relates to an apparatus and method for distinguishing the size of a particle. More specifically, the invention relates to apparatuses and methods for screening the relative size of a particle within a capillary.

TECHNICAL BACKGROUND

Microbes are a common cause of illness and death. In order for medical professionals to diagnose and treat an illness it is often necessary to identify the disease causing agent. Moreover, identifying the cause of an outbreak of disease allows steps to be taken to prevent the spread of the disease.

Microbes are sometime identified based on physical characteristics such as size, shape, colony type, and staining characteristics. While such physical characteristics can be used to eliminate some of the possible disease causing agents, it is often not possible to identify a microbe based on these characteristics alone. For example many species of bacteria are further classified into strains. Some members of the species can be harmless or even beneficial microbes, while others may be pathogenic.

Because the disease causing strains have a gene or genes that render them pathogenic, DNA analysis can be used to identify these strains. The DNA analysis can provide a positive identity of a pathogenic organism. However, the amount of information provided is limited, and the process can take a considerable amount of time. When the purpose of identifying the microbe is to treat a disease or prevent its spread the DNA analysis may take too long to be useful.

Amplified Fragment Length Polymorphism (AFLP) and strain-specific polymerase chain reaction (PCR) analyses are the methods used for determining the identity of microbes. These procedures provide significantly more information than standard DNA analysis and are more rapid and less expensive than extensive DNA sequencing. AFLP analysis can be used for rapidly characterizing unknown pathogenic species and strains, thereby providing valuable information for developing a therapeutic response to an outbreak thereof Strain-specific PCR analysis can rapidly identify a previously studied threat species, even if the sample is present in a complex sample mixture. Both methods require further analysis of the reaction results to determine the size of the DNA fragments. Simple detection of the presence or absence of the fragment is insufficient. The time required to complete the reaction analysis is presently between 15 and 20 minutes. However, size analysis is currently conducted using an automated DNA sequencer. The gel procedure requires approximately three hours to complete, plus additional time to set up the sequencing unit and download the resulting data. When faced with the potential or actual release of a biothreat agent, it is important to obtain the genetic information about the released organism in a significantly shorter time period. It is also important to be able to conduct analyses in a field laboratory using affordable apparatus. Flow cytometry analysis does not allow resolution of such small fragments. Commercial capillary electrophoresis sequencers have sufficient resolution, but have a high cost and are not suitable for rapid fragment size determination.

Currently, DNA size analysis requires approximately three hours to run on a gel, plus additional time to set up the sequencing unit and download the data. Flow cytometry analysis does not resolve 100 to 500 base pair (bp) fragments with 1 bp resolution which is required. Commercial capillary electrophoresis sequencers that can resolve 1 bp are costly and do not permit size determination.

Capillary electrophoresis is a powerful analytical technique that can be used to separate and detect a number of analytes according to their charge. Traditionally, electrophoresis has been practiced on slab gels. However, the use of capillaries introduces a number of advantages including small sample and electrolyte volumes, high efficiency separations, and small instrument size. The capillary systems are also amenable to miniaturization.

In capillary electrophoresis, an electrical field is applied along the length of a fused silica capillary filled with a buffer. Typically, particle samples are introduced at the anode and are carried towards the cathode by the electroosmotic movement of the electrolyte and the electrophoretic movement of the analyte ions. The sample is separated according to the charge to size ratio of the analyte ions.

The separated sample is detected at some optimal fixed point in the capillary. A number of detection schemes are used in capillary electrophoresis including spectroscopic techniques such as UV-Vis absorbance, fluorescence, and raman; mass spectrometry; and electrochemical detection. Separations can be performed on analyte samples including charged particles such as small organic acids and bases, proteins, peptides, amino acids, and nucleic acids. Neutral molecules can also be separated with a special form of capillary electrophoresis called micellar electrokinetic chromatography. Because the entire sample must migrate past the detection window, the capillary electrophoretic systems tend to be long and require significant time for a good separation of particles.

In light of the foregoing, it would be a significant advancement in the art to provide a device that could rapidly separate and detect particles in a sample solution. It would be a further advancement if the device could be produced inexpensively. It would be a further advancement if the device were amenable to a high throughput system and miniaturization. It would be a further advancement if the device used capillary electrophoresis. Such a device is disclosed and claimed herein.

BRIEF DESCRIPTION THE INVENTION

The present invention relates to a device and method for electrophoretic separation and detection of particles. Such particles may include but are not limited to nucleic acids, proteins, inorganic ions, organic ions, or neutral species. The device has a separation channel in which the particles are loaded. The particles may be separated by applying a charge along the length of the separation channel. After a period of time, a detector may be activated to determine the location of the separated particles in the separation channel.

The separation channel may be a capillary having a first end and a second end. The capillary is filled with an electrolyte buffer solution formulated for electrophoresis. The buffer-filled capillary is connected adjacent the first end to a first buffer reservoir and adjacent the second end to a second buffer reservoir. The buffer solution may contain tris-boric acid EDTA hereinafter, TBE, potassium tartrate, tris-acetate EDTA, hereinafter TAE, and a gel sieving material. The gel may be added to mechanically separate particles with a relatively constant charge to ionic radius such as oligonucleotides. Such sieving materials may include but are not limited to poly(ethylene glycol), poly(vinyl alcohol), hydroxy propyl methyl cellulose, hydroxyethylcellulose, linear polyacrylamide and/or poly(vinylpyrrolidone). If the buffer solution has too high of a viscosity, the solution will not flow properly through the capillary during loading, however, too low of a viscosity may not allow optimal separation of the particles. Using the above gel sieving materials in a mixed mode at a concentration in the range from about 0.1% to about 5% will create a workable viscosities in the range of about 0.5 cp to about 50 cp at room temperature.

A sample of particles to be separated may be loaded adjacent the first end of the capillary. An electrical source is used to apply a voltage along the capillary. Generally a voltage in the range of about 4,000 V dc to about 20,000 V dc may be used. The particles within the capillary migrate under the influence of the voltage in the direction of the second end of the capillary. As the particles migrate they are separated.

After the voltage has been applied for a period of time, the capillary may be scanned by a detector to determine the location of the separated particles. The detector may scan the capillary at more than one position. Because the detector can scan more than one position on the capillary, the time required to separate and detect the location of the particle is reduced, compared to conventional fixed detector instruments.

The detector may use fluorescent technology to detect the particles. For example, a fluorescent label may be attached to the particles prior to loading the particles in the capillary. When the particles have been separated, an excitation source such as a laser, may direct an excitation beam on the capillary. The excitation source may be scanned along the capillary to direct the excitation beam on more than one position along the length of the capillary. The scanning of the excitation source along one or more capillaries is hereinafter referred to as rastering. Rastering the beam along the part or all of the length of the capillary shortens the time required to separate and detect the particles. The fluorescent labels on the particle emit fluorescent light after excitation with the beam.

The excitation beam may be configured to allow for optimal detection and resolution of particles. An excitation beam may bleach the fluorescent tags if the beam's intensity is too great. Additionally, if the beam is too weak, the fluorescent tags may not emit enough light to be detected. A beam with a power in the range of about 1 mW to about 1000 mW will allow the tags to fluoresce while minimizing bleaching. The excitation beam may also be configured with a width sufficient to allow the light detector to distinguish between particles of different sizes. A beam width in the range from about 5 $\mu$m to about 1000 $\mu$m can be used to excite the fluorescent tags.

A light detector is positioned to detect the fluorescence and record the position of the beam on the capillary when fluorescence is emitted. The position of the beam on the capillary when fluorescence is detected can be used to determine the position of a fluorescing particle within the capillary. The light detector may be low-level light detection electronics such as photomultipliers, photodiodes, and CCD cameras. The light detector may be connected to a computer to record and determine the position of the fluorescing particle.

The capillary may be covered with a coating to create a light waveguide. The light waveguide retains the fluorescent light within capillary and directs the flourescent light toward the ends of the capillary. A light detector positioned adjacent either end of the capillary may detect the fluorescence. A coating with low a refractive index may optimally retain the fluorescent light. Generally, a coating with a refractive index between about 1.1 and 1.5 is used A coating with a refractive index of about 1.3 is presently preferred. Polytetrafluoroethylene coatings such as Teflon® AF manufactured by DuPont have a sufficiently low refractive index.

A fiber optic may be coupled end-on to the capillary. The fiber optic allows the light detector to be positioned somewhat distantly from the end of the capillary. The fiber optic can be made of a material that is optimized for transmission of the wavelength of the light to be detected. Generally the wavelength of the light emitted from the fluorescent tags is in the range of about 200 nm to about 1000 mn An optical filter may be placed between the capillary and the light detection electronics. The filter is selected such that the fluorescent light passing through the filter is maximized while background light such as the light of the excitation laser is minimized. The optical filter assembly may have a high band pass filter for filtering light with a wavelength greater than about 500 nm and a notch filter for filtering the light of the excitation beam. In other configurations, the optical filter may be a narrow band pass filter which filters light other than the light with a wavelength corresponding to the wavelength of the light emitted from the fluorescent label ±10 nm. Even other configurations may use a light spectrometer to resolve the fluorescent light according to its characteristic wavelengths and detect the resolved light.

The light detector may be configured to detect and distinguish between more than one color of flourescent light. In this manner different particles may be labeled with fluorescent tags which fluoresce at different wavelengths. The detector will detect the different colors of light and determine the position within the capillary of the differently labeled particles. Such a configuration may be useful in such applications as sequencing a nucleic acid.

The capillary typically has a length in the range from about 5 cm to about 100 cm. A length of less than about 20 cm may allow for sufficient separation of most particle that may be used with the device. A capillary length of about 10 cm may be used to create a compact capillary electrophoretic device without compromising the ability of the device to separate and detect long DNA fragments.

The separation and detection device may be adapted for a high throughput system by the addition of one or more capillaries. Such multi-capillary devices will allow for rapid separation and identification of particles. These additional capillaries can be configured and attached to the device as the single capillary discussed above. Such a multi-capillary system may facilitate the sizing of particles. For example, a particle of unknown size can be fluorescently labeled and loaded into a first capillary. A sample of particles of known sizes can also be fluorescently labeled and loaded into a second capillary. A voltage is applied along the capillaries for a period of time causing the particles to migrate within the capillaries. The capillaries are then rastered with an excitation beam, and the position of the particles determined. The location of the particle of unknown size may be compared to the sample of particles of a known size to determine the size of the unknown. Additionally, when the device is used to sequence a nucleic acid, the plurality of capillaries increases the speed at which a long nucleic acid segment can be sequenced.

The present invention also relates to a method for separating and sizing of particles by using the short channel capillary electrophoresis device of the present invention. A sample of particles to be separated and sized is obtained and fluorescently labeled. The fluorescently labeled particles are loaded into a device of the present invention with one or more capillaries. A voltage is applied along one or more capillaries for a period of time. The excitation beam is rastered onto the one or more capillaries. The detection of the fluorescence from the excited particles is monitored and recorded. The position of the excitation beam on the capillary when fluorescence is detected can be used to determine the position of the particles in the capillary and relative size of the particles as compared to known size standards.

The voltage is left on for a time sufficient to allow for adequate separation of the particles. It has been found that a period in the range from about 8 minutes to about 18 minutes allows for the particles to be separated enough to be distinguished by the detection system. Additionally, a period of less than about 15 minutes may be used with most particles, while generally a period of about 12 minutes may be used.

The device of the present invention can also be used with methods for sequencing a nucleic acid. For example a sample of DNA to be sequenced is obtained. The DNA sample is then run in standard a dideoxy sequencing reaction. The sequencing reaction has four separate reaction mixtures with a different dideoxy nucleotide for each standard nucleotide type. A distinct flourescent label is added to each of the four reaction mixtures. The reaction mixtures are run to form four separate reaction product. The reaction products are pooled and loaded into the apparatus of the present invention with a light detector capable of detecting and distinguishing between the fluorescence of the four fluorescent tags. A voltage is then applied across the one or more capillaries of the device. The excitation beam is rastered on the capillaries and the fluorescent light collected in the light detector is monitored. A comparison of the position of the excitation beam on the capillary to the color of light detected by the light detector may be used to determine the position and type of a corresponding nucleotide within the DNA sample, thus producing a DNA sequence.

DESCRIPTION OF THE DRAWINGS

A more particular description of the invention briefly described above will be rendered by reference to the appended drawings and graphs. These drawings and graphs only provide information concerning typical embodiments of the invention and are not therefore to be considered limiting of its scope.

DETAILED DESCRIPTION OF THE INVENTION

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the apparatus, system, and method of the present invention, as represented in FIGS. 1 through 6, is not intended to limit the scope of the invention, as claimed, but is merely representative of presently preferred embodiments of the invention Referring to FIG. 1, a capillary electrophoretic device for separating and detecting particles is generally designated as 10. The device 10 can separate particles including but not limited to nucleic acids, proteins, inorganic ions, organic ions, and neutral species. A capillary 12 is filled with an electrolyte buffer solution 17. The capillary 12 functions as a separation channel wherein the particles are electrophoretically separated. A voltage is applied across the capillary 12 by an electrical source 30. As the voltage is applied, the particles migrate from a first end 14 of the capillary 12 toward a second end 16 of the capillary. The particles continue their migration until the electrical source 30 is shut off or disconnected from the capillary 12. A detector 38 is used to scan the length of the capillary 12 to detect particles within the capillary 12. The separation is allowed to proceed until the first analyte reaches the prepositioned detector. The separation is then stopped and the detector 38 scanned along the length of the capillary. The location of the particles can be ascertained by recording the position of the detector 38 when the particles where detected.

Figure 1:
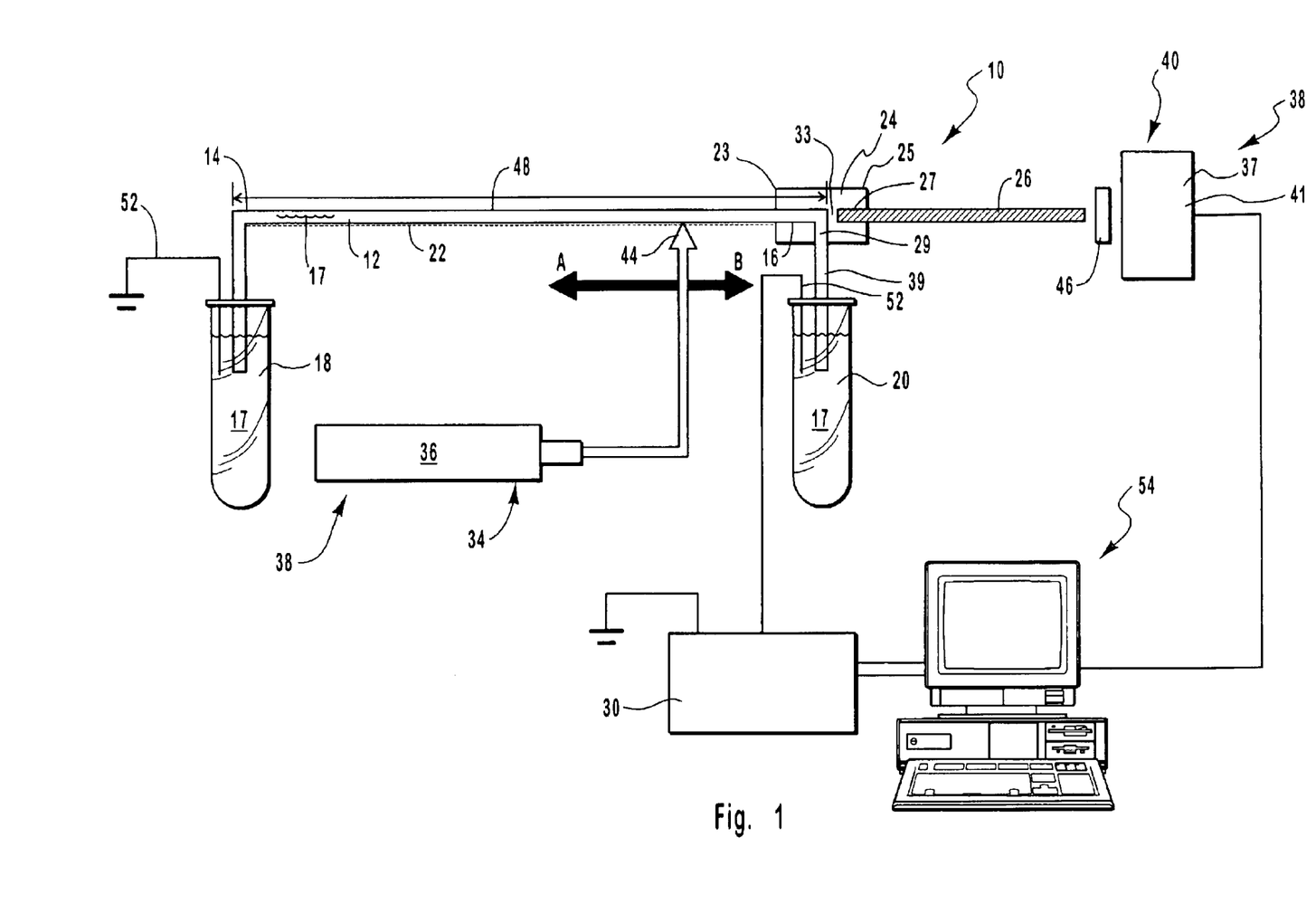
FIG. 1 is a perspective view of one embodiment of a device of the present invention.

The capillary 12 is dimensioned to create a compact electrophoretic device 10. In general the capillary 12 has a length 48 in the range from about 5 cm to about 100 cm. Capillaries 12 with a length 48 in the range from about 10 cm to about 50 cm have been used to effectively separate the particles. It is presently preferred that the length 48 of the capillary 12 be about 10 cm. The capillary 12 has an inside diameter in the range from about 20 $\mu$m to about 150 $\mu$m. Efficient, reproducible separation and detection of the particles is possible even with these small dimensions because of the detector 38 is rastered along the capillary 12.

A range of voltages can be used with the electrophoretic device 10. In general the voltage applied is in the range from about 4,000 V to about 20,000 V dc. A voltage of about 11,000 V dc is used in one presently preferred configuration of the electrophoretic device. The voltage creates a current within the capillary 12 in the range from about 1 $\mu$A to about 60 $\mu$A. A current of about 10 $\mu$A has been used to separate the particles efficiently. Moreover, the capillary 12 does not have to be precoated to deactivate the inner surface.

The period of time that the voltage is left on should be sufficient to allow for adequate separation of the particles. It has been found that a period in the range from about 8 minutes to about 18 minutes allows for the particles to be separated enough to be distinguished by the detection system. Additionally, a period of less than about 15 minutes may be used with most particles. A period of about 12 minutes has produced adequate separation of the particles.

A first buffer reservoir 18 is in fluid communication with the first end 14 of the capillary 12. A second buffer reservoir 20 is also in fluid communication with the second end of the capillary 12. The buffer reservoirs 18, 20 present a convenient location for the attachment of electrodes 52. As the particles migrate under the electrical current, a small amount of buffer solution may also flow along the capillary. The buffer reservoirs 18, 20 ensure that the capillary 12 is constantly filled with buffer solution 17.

The particles can be loaded into the capillary 12 by electrophoretic injection. The first buffer reservoir 18 is removed and replaced with a reservoir containing a sample of particles. The electrical source is activated to apply a voltage across the capillary for a short period of time. A period of about 15 seconds is sufficient to cause the sample to be injected into the capillary 12. Once the sample of particles is loaded, the buffer reservoir 18 can be replaced and the particles separated.

The electrolyte buffer 17 can be chosen from the various buffers generally used with electrophoretic systems. The electrolyte buffer 17 is typically tris-boric acid EDTA, hereinafter TBE, potassium tartrate, or tris-acetate EDTA, hereinafter, TAE. The electrolyte salt is generally used at a concentration in the range of about 0.1× to about 2×. In a presently preferred embodiment the concentration of the electrolyte salt is about 0.5×.

Separation of DNA fragments and other oligonucleotides presents a special challenge to capillary electrophoresis because oligonucleotides have relatively constant charge to ionic radius with fragment size. Thus introducing DNA fragments into free zone capillary electrophoresis systems usually will result in no separation. However, the use of electrophoresis as a method of transporting DNA fragments is quite advantageous because flow occurs under laminar conditions with relatively constant velocity across the migration zone in the capillary. Separations of DNA in a capillary electetrophoretic system is accomplished through mechanical sieving.

In order to accomplish the mechanical separation of the DNA fragments, the electrolyte buffer solution 17 further contains a gel sieving material in distilled water. The gel sieving material is composed of cellulose polymers or their derivatives such as poly(ethylene glycol), poly(vinyl alcohol), hydroxy propyl methyl cellulose (HPMC), hydroxyethylcellulose, or linear polyacrylamide. The cellulose polymers or derivatives are combined with a low viscosity surface coating material such as poly (vinylpyrrolidone) (PVP). The sieving material should have a viscosity that allows the buffer solution to be readily added and removed from the capillary while coating the capillary surface. Optimally, the viscosity is in the range of about 0.5 cp to about 50 cp. A viscosity of about 5 cp is used in one presently preferred embodiment. Typically the sieving polymer is added at concentrations of about 0.1% to about 2%. It has been found that HPMC at a concentration of about 0.5% efficiently functions as a mechanical sieve. Generally, PVP is added at concentrations of about 0.1% to about 5%. A concentration of about 5% PVP is presently preferred in one configuration.

The capillary 12 is coated with a coating 22 having a low refractive index. The coating 22 transforms the capillary 12 into a light waveguide which retains light within the capillary and does not exclude the excitation light—from entering the capillary. The light is directed toward the ends 14, 16 of the capillary. For the coating to transform the capillary into a light wave guide, the coating has a refractive index number lower than the refractive index of the material from which the capillary is made and lower than the refractive index of the separation medium. Generally, the capillary is made from fused quartz or fused silica which have a refractive index number of about 1.5. Thus, a material with a refractive index number in the range of about 1.1 to about 1.4 is used. A material with a refractive index number of about 1.31 is presently preferred. Polytetrafluoroethylene materials such as Teflon® AF manufactured by DuPont have a sufficiently low refractive index.

The detector 38 uses fluorescence detection to determine the position of the particles within the capillary 12. Fluorescence detection is a sensitive detection method that can be used with capillary electrophoresis. For example the separation assay represented by FIG. 5 was performed using TO-PRO-3 intercalating dye (642/661 Ex/Em). This dye can be easily excited with a small HeNe laser at 635 nm. Using TO-PRO-3 allows the system to be quite sensitive, however, the sensitivity of the system can be improved dramatically by using other dyes such as PicoGreen (498/520 Ex/Em). Excitation with an argon ion laser at 488 nm may also be used, however the argon laser can be bulky and cumbersome. Using diode lasers which emit at 500 nm can allow for fluorescent detection of particles while using a smaller laser. Fluorescence detection is generally performed by collection optics positioned at normal angles to the capillary. High aperture optics and mirrors can be used to maximize light collection.

As illustrated in FIG. 1, an excitation source 34 such as a laser 36 or other light source is positioned perpendicular to the capillary 10. The excitation source 34 is mounted to a stage (not shown) which allows the excitation beam 44 to be scanned or rastered in a first direction A or a second direction B along the length of the capillary 12. The particles to be analyzed are tagged with a fluorescent label before they are injected into the capillary 12. The excitation source 34 is tuned to the excitation frequency of the fluorescent tag on the particles. When the excitation beam 44 contacts the fluorescent labels they emit fluorescent light. Because of the coating 22, the fluorescence is contained within the capillary 12 and directed toward the ends thereof 14, 16 where the light can be detected by a light detector 37. The light detector 37 is coupled to a computer 54 which determines the position of a particle within the capillary 12 by analyzing the position of the excitation beam 44 on the capillary 12 and the fluorescence signals.

The light of the excitation beam 44 is focused on the capillary 12 to achieve the maximum light intensity without causing the fluorescent tags to photo-decompose. The focusing of the beam 44 on the capillary also minimizes the width of the excitation beam. Because the minimized beam 44 directs light onto only a very small portion of the capillary at a given time, the device 10 can detect a small separation distance thereby maximizing the detection efficiency of the device 10.

The power of the excitation beam 44 can be optimized to provide maximum fluorescing of the fluorescent tags while minimizing the background light transmitted through the capillary 12, An excitation beam 44 with a power in the range from about 1 mW to about 100 mW allows for sufficient fluorescing of the tags while minimizing the interfering background light within the capillary. In a presently preferred embodiment of the electrophoretic device 10, the excitation beam has a power of about 30 mW.

To achieve good separation efficiencies for DNA fragments it is preferable to set up a detection optics system that can allow for a separation efficiency of about 0.1 to about 100 million theoretical plates. The overall achievable separation efficiency is a function of the width of the excitation beam and the separation length that is being used and imaged. The width of the excitation beam should be in the range from about 5 μm to about 1000 μm for a separation length of from about 5 to about 100 cm. It is presently preferred that the width of the beam 44 be about 50 μm or less for a separation length of about 10 cm. The excitation beam 44 is moved along the capillary 44 in a series of steps small enough to distinguish between the separated particles. A step approximately equal to the width of the excitation beam 44 allows for adequate distinction of particles. The excitation beam 44 is moved along the capillary at a rate slow enough to maximize the signal to noise ratio, yet fast enough that the separation plus detection time is minimized. The detection time per laser step along the capillary is 1–1000 ms, with the preferred step duration being only 5 ms.

A connector 24 is coupled to the capillary 12 near the second end 16 of the capillary 12. The connector has a first end 23 and a second end 25. The connector 24 has a channel 27 that runs from the first end 23 of the connector 24 to the second end 25. The channel 27 is proportioned so that the capillary 12 fits, snugly within the channel 27 without leaking buffer solution 17. The capillary 12 is inserted within the connector 24 to approximately the midpoint of the connector 24. A second channel 29 is formed in the connector 24 in which a tube 39 is inserted to fluidly connect capillary 12 to the buffer reservoir 20. A fiberoptic 26 is inserted within the first channel 27 to the point of almost contacting the capillary 12. The fiberoptic 26 is selected to optimize the wavelength of light to be detected. Generally a fiberoptic 26 optimized for light in the range from about 200 nm to about 1,000 nm is used. In a presently preferred configuration, the fiberoptic is optimized for light with a wavelength between about 500 nm to about 600 nm.

A small separation distance 33 is left between the fiberoptic 26 and the capillary 12 to allow the capillary 12 to be in fluid communication with the buffer reservoir 20 while preventing the fluorescence from escaping. An optimal separation distance 33 depends on the numerical aperture of the capillary waveguide 12 and the fiberoptic 26. Generally this separation distance 33 is in the range from about 0.1 mm to about 1.5 mm. In a presently preferred embodiment, the separation distance 33 is optimized at 0.5 mm. The distance 33 can be important to efficient light collection, and fluid flow of the system. If the distance 33 is too large the fluorescence will not accurately be detected. If the distance is too small the fluid will not flow properly.

This arrangement allows the use of a fiberoptic 26 coupled end-on to the capillary 12. With this configuration, the capillary 12, with its low refractive index coating, acts as a liquid core waveguide trapping and directing the fluorescent light longitudinally toward the fiberoptic 26. The fiberoptic 26 directs the light into low-level light detection electronics 40 which can detect and signal a computer 54 of the presence of fluorescence. Suitable low-level light detection electronics 40 may include photomultipliers, photodiodes or CCD cameras. Because the capillary 12 serves as a light wave guide, the fiberoptic 26 and low-level light detection electronics 40 can be positioned at one or both ends of the capillary 12. In the illustrated configuration, a single photo multiplier 41 is used.

An optical filter 46 is positioned between the fiberoptic 26 and the light detection electronics 40 to prevent incident light from the excitation source 34 from reaching the detection electronics 40. The filter 46 is selected such that it maximizes the fluorescent light while minimizing the background light from the excitation beam hitting the detector. The optical filter system can be a combination of a high band pass filter 46, for example greater than about 500 nm, with a notch filter 46 at the wavelength of the excitation beam for example about 488 nm. Alternatively, the filter 46 may be a narrow band pass filter 46 at the emission wave length corresponding the fluorescence of the fluorescent tags. For example a narrow band pass filter in the range of about 520 nm plus or minus about 10 nm has been used. Other methods of filtering light such as a prism, or light spectrometer may be also used.

Figure 2:
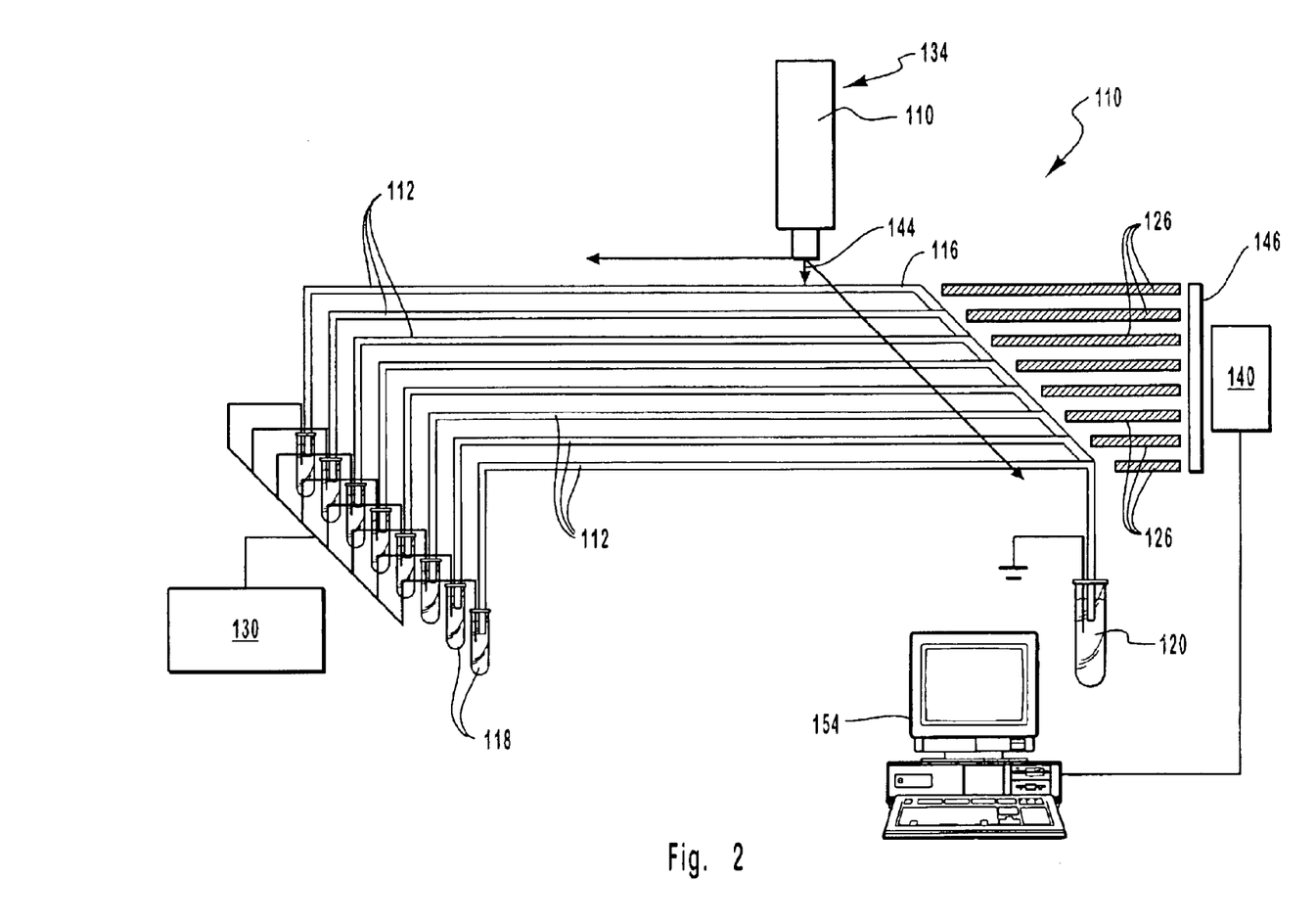
FIG. 2 is a perspective view of an alternative embodiment of the device of the present invention.

Referring now to FIG. 2, a capillary electrophoretic system for high throughput analysis is generally designated 110. The high throughput is made possible by the addition of one or more capillaries 112. Such multi-capillary devices 110 allow for rapid separation and identification of particles. The speed of separation, detection, and sizing of particles is increased because multiple samples can be run simultaneously.

The capillaries 112 are configured and attached to the device 110 much like the single capillary 12 discussed above. The particles are loaded into multiple capillaries 112 and a voltage applied from an electrical source 130. After the particles are sufficiently separated, the voltage is shut off and the excitation source activated to cause the particles to fluoresce. The excitation source 134 can be a laser 136 or other light source as discussed above. The excitation source 134 is mounted on a X-Y stage so that the single beam 144 can be independently directed onto each of the capillaries 112.

Multiple fiberoptics 126 are coupled to the second ends 116 of the capillaries 112 as with the single capillary device 10. The fiberoptics 126 direct the fluorescence toward light detection electronics 140. Thus, a single photomultiplier can function to detect the light from all of the capillaries 112 and direct the information into a computer 154. A filter 146 can also be provided to reduce the incident light transmitted to the light detection electronics 140.

The present invention also relates to a method for separating and sizing of particles by using the short channel capillary electrophoresis device 10, 110 of the present invention as illustrated in FIGS. 1 and 2. A sample of particles to be separated and sized is obtained and fluorescently labeled. The fluorescently labeled particles are loading into a device 10, 110. A voltage is applied across the one or more capillaries 12, 112 for a period of time. The excitation beam 44, 144 is rastered onto the one or more capillaries 12, 112. The light detector 40 collects the fluorescence from the excited particles. The position of the excitation beam 44, 144 on the capillary when fluorescence is detected is used to determine the position of the particles in the capillary 12, 112 and the relative size of the particles. A sample of particles of known size can also be loaded with the unknown sample. Thus, the position of the unknown particles can be compared to the position of the known particles to determine the actual size of the unknown particles.

The capillary electrophoretic device 10, 110 can be used to sequence DNA by simply adding three more photomultipliers and filtering sets or using a light spectrometer. DNA to be sequenced is run in a standard dideoxy sequencing reaction. A separate reaction mixture is set up for each of the standard nucleotide types, and contains one dideoxy nucleotide type. Each reaction mixture contains a distinct fluorescent label, thus a label is created for each of the four standard nucleotide types. The reaction mixtures are run to form four separate reaction products. The reaction products are pooled and loaded into the apparatus of the present invention 10, 110. Each of the photomultipliers is selected to detect one of the four fluorescent tags. A voltage is then applied across the one or more capillaries 12, 112 of the device. The excitation beam 44, 144 is rastered on the capillary, and the fluorescent light is collected by the photomultipliers. A comparison of the position of the excitation beam on the capillary to the color of light detected by the photomultipliers is used to determine the position and type of a corresponding nucleotide within the DNA sample. Photomultipliers are used because they are inexpensive and very sensitive, however, other light detection systems such as CCD cameras, photo diodes and light spectrometers may also be used. The fiberoptic 26 that couples the light from the separation channel to the detector can be divided from the detection channel to direct light to one or more light detectors.

EXAMPLES

The following examples are given to illustrate various embodiments which have been made with the present invention. It is to be understood that the following examples are not comprehensive or exhaustive of the many types of embodiments which can be prepared in accordance with the present invention.

Example 1

Electrophoresis

Electrophoresis takes advantage of the differences in the movement of ions in an electrical field, in solution. The electrophoretic velocity ($v_{ep}$) for ions in a fluid with viscosity ($\eta$) and in an electrical field (E) varies according to the charge state (q) and ionic radius (r) of the ion according to the equation:

$$v_{ep} = \frac{5/3q}{\pi r \eta} E$$

Figure 3:
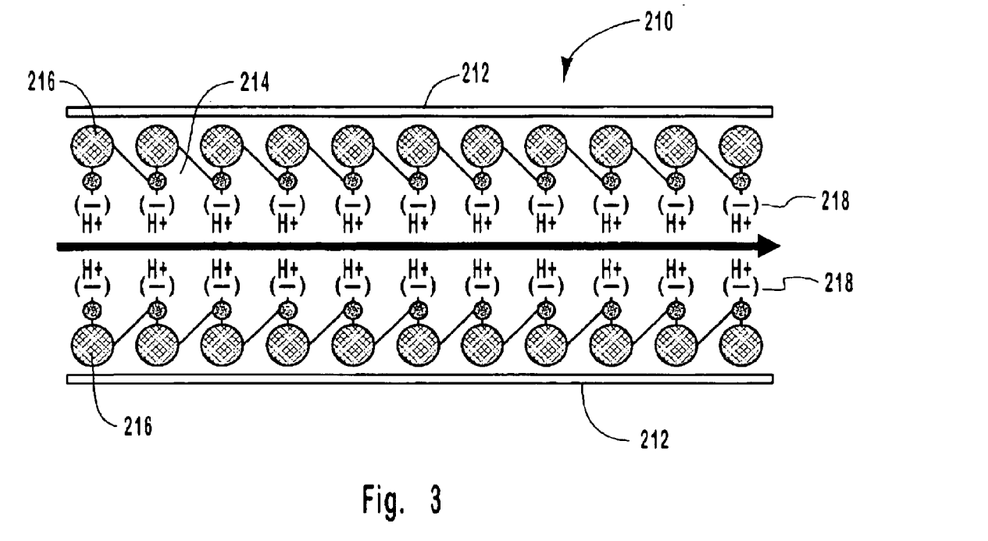
FIG. 3 is a schematic representation of the ionic double layer formed at a capillary wall constituting the major influence in the movement of bulk fluid, electroosmotic flow, towards the cathode.

Referring to FIG. 3, when practiced in a fused silica capillary 210, the electrophoresis process is also influenced by a bulk movement of the electrolyte fluid in the capillary 210. This movement is caused by the formation of an electrical double layer 214 at the walls 212 of the capillary 210. The cause of this double layer 214 is based on the existence of negative silanol charges 216 at the fused silica surface. These fixed silanol 216 charges attract positive charges 218 from the fluid. Overall there will also be an attraction of the positive charges 218 towards the cathode causing the bulk fluid movement called electroosmotic (or endoosmotic) flow.

The electroosmotic velocity is given by the potential arising from the charge on the wall (ξ), the solution's dielectric constant (∈), the viscosity of the liquid (η), and the electrical field (E), according to the equation:

$$v_{eo} = \frac{\varepsilon \xi}{4\pi \eta} E$$

The overall velocity of the analyte in such a system is given by the summation of these two vectors: $v=v_{ep}+v_{eo}$. For DNA analysis it is advantageous for the electroosmotic vector to be 0 or negligible. In that way, DNA particles may migrate only under the influence of their charge, which is negative, and not be opposed by the positive electroosmotic flow of the solution. This is achieved by introducing a surface deactivating agent, e.g., poly(vinylpyrrolidone).

Example 2

Separation of a DNA Ladder Using TBE Buffer

Figure 4:
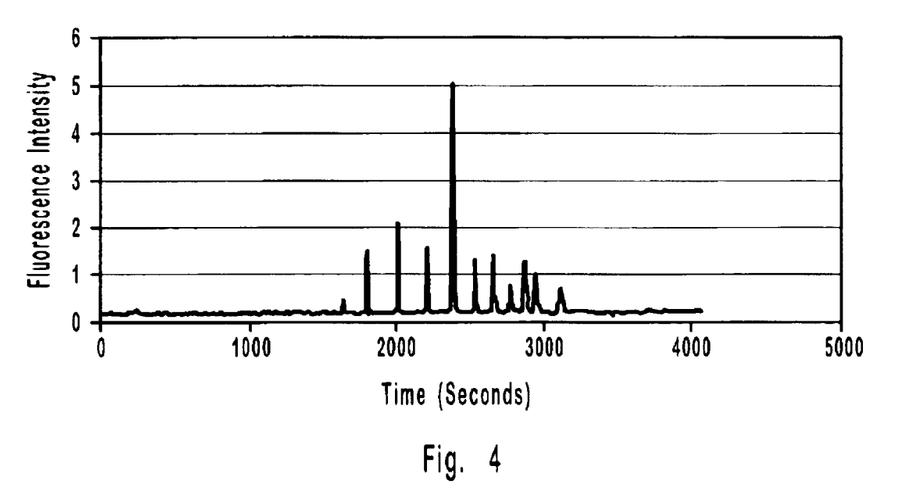
FIG. 4 is a graph representing the separation of a 100 to 1,500 bp DNA ladder using the mini-CE apparatus in a 50 cm column. Time axis in seconds.

A sample of particles was loaded into a capillary electrophoretic device of the present invention. The capillary was filled with TBE buffer with a gel sieving material. The gel sieving material was present at a concentration between about 0.5% and about 1%. The separation was performed on a device with about a 25 cm capillary length. As seen in FIG. 4, the separation was excellent. The separation of FIG. 4 was performed in about 50 minutes. However separations can be achieved in less than 10 minutes using a 25 cm column but with decreased resolution at the large fragment end. Nevertheless separations of PCR products that achieve +/−5 base pair resolution at fragment lengths below 500 bp, in five minutes have been achieved.

Example 3

Separation and Detection of a 1,500 bp DNA Ladder

Figure 5:
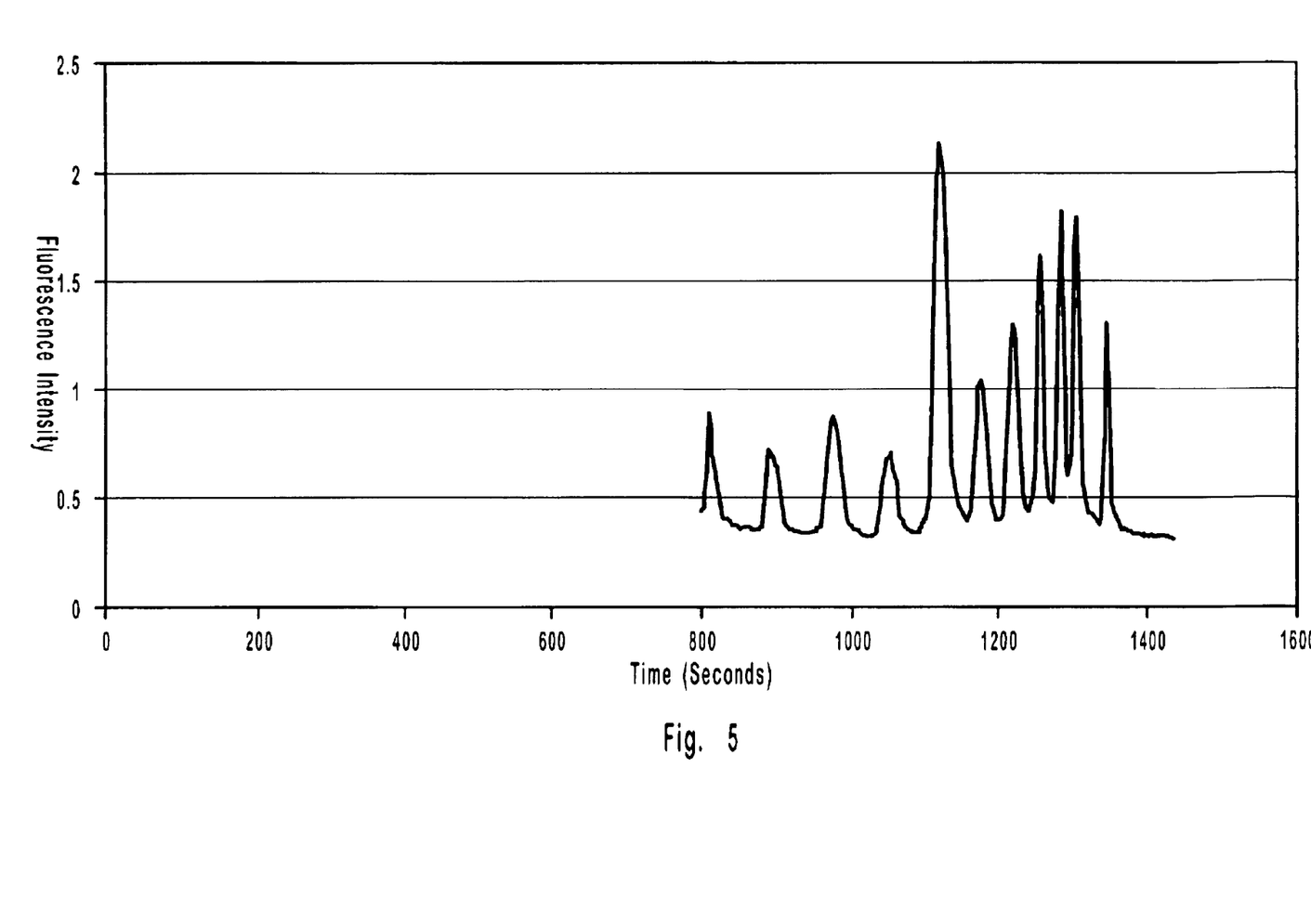
FIG. 5 is a graph representing the separation of a 1,500 bp DNA ladder detected with a fixed fluorescence detector.

A 1,500 bp DNA ladder was obtained and loaded into a standard capillary electrophoretic device with a stationary detection beam. A current was applied across the capillary. The particles were detected as they moved past the detection window of the device. As seen in FIG. 5, the separation and detection of the 1,500 bp DNA ladder took about 1,400 seconds or over 23 minutes.

Figure 6:
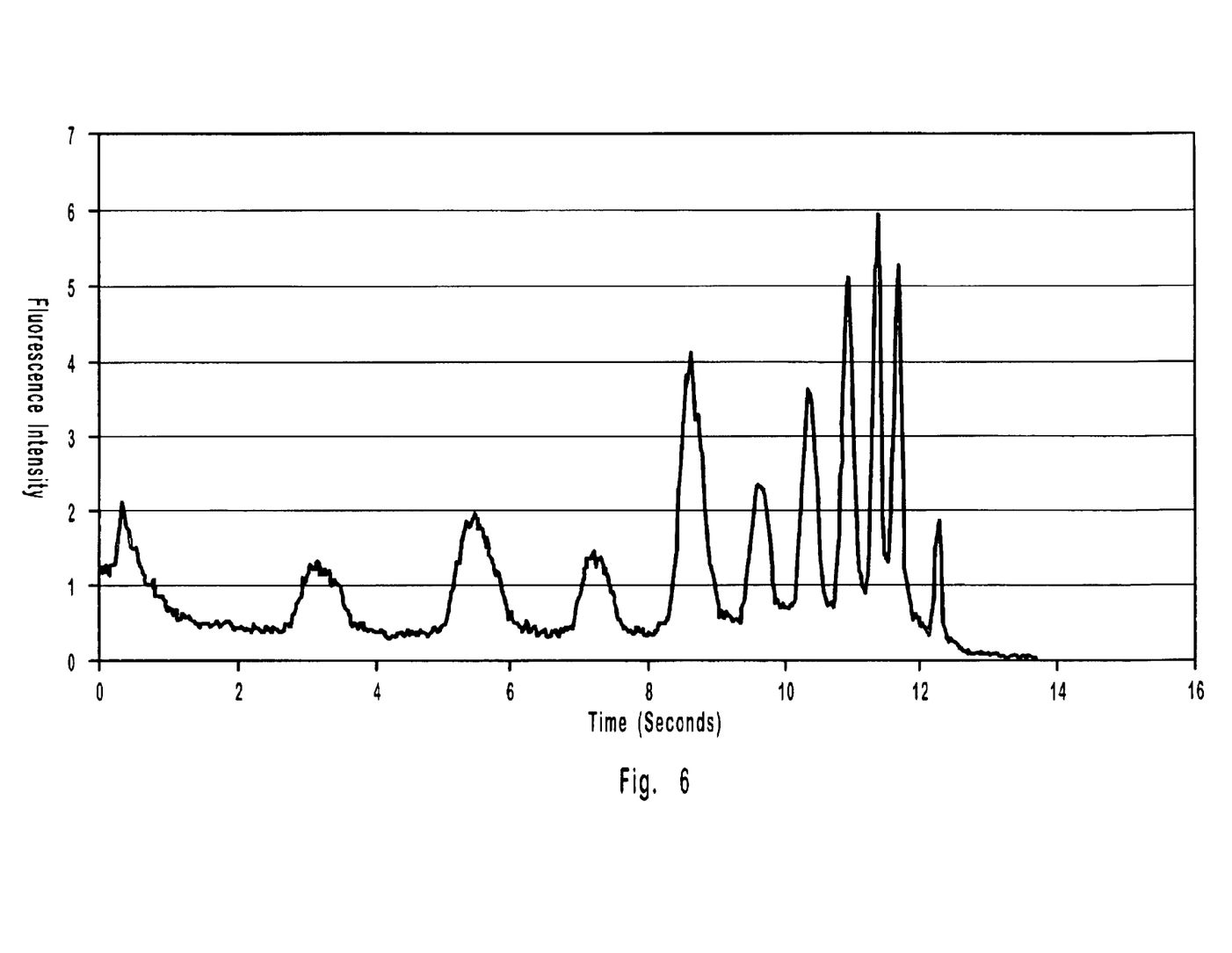
FIG. 6 is a graph representing the detection of a 1,500 bp DNA ladder detected 800 seconds after start of separation by scanning the excitation laser along the length of the capillary.

A 1,500 bp DNA ladder was also loaded into the capillary electrophoretic device of the present invention. After a period of about 13 minutes, the migration of the particles was terminated by disconnecting the voltage. The detection beam was moved along the length of the capillary to image the complete electrophoretic separation of the particles. In this manner, each separated fragment does not have to pass by a detection window, but the complete separation channel becomes the detection window. The detection process took only about 10 seconds longer of additional time. As seen in FIG. 6, the device of the present invention decreases the amount of time previously required to separate and detect DNA fragments. The device also needed only about 13 cm of capillary length to fully separate the DNA ladder.

SUMMARY

In summary, the use of multi-capillary electrophoresis technology for inexpensive, sensitive and high-throughput DNA fragment and chemical sizing is described. The device can separate and detect particles within a short capillary. The addition of a sample of particle of known size will allow the actual size of the particles to be rapidly determined. The invention is also useful for multi-color DNA sequencing applications. A sample to be analyzed is introduced into one end of an electrophoresis capillary, and a voltage is applied longitudinally along the capillary wall which results in electrophoretic separation of the component materials in the sample. The capillary also functions as a liquid-core waveguide. Detection of fluorescence resulting from the interaction of light introduced through the capillary wall with the component materials is then accomplished at the end of the capillary. Excitation of the separated sample components in the capillary may be achieved at any point in the capillary, which permits the instantaneous visualization of the entire electrophoregram. By controlling component movement through the capillary, samples can be removed for further analysis using mass spectrometry or DNA sequencing. The technology will allow analyses to be conducted in a field laboratory without using large and expensive equipment.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A device for separating and detecting particles comprising:
   a capillary having a first end and a second end, the capillary filled with a buffer solution, the capillary having a coating that transforms the capillary into a light wave guide;
   an electrical source for applying a voltage across the capillary, the voltage causing the particles to travel from a first location within the capillary to a second location within the capillary;
   an excitation source for rastering an excitation beam onto the capillary along part or all of the length of the capillary, such that when a fluorescently labeled particle is positioned within the capillary, the fluorescently labeled particle emits light after excitation with the excitation beam; and
   a light detector positioned at one of the first or second ends of the capillary to collect fluorescent light emitted from the excited fluorescently labeled particles for determining the location of particles within the capillary based upon the location of the rastered excitation beam.

2. The device of claim 1, further comprising a first reservoir in fluid communication with the first end of the capillary, the first reservoir configured to contain buffer solution and a second reservoir in fluid communication with the second end of the capillary, the second reservoir configured to contain buffer solution.

3. The device of claim 1, wherein the light detector further comprises a fiber optic coupled end-on to the capillary.

4. The device of claim 3, wherein the light detector comprises low-level light detection electronics.

5. The device of claim 3, wherein the coating on the capillary that transforms the capillary into a light wave guide directs the fluorescent light toward the light detector.

6. The device of claim 1, wherein the coating has a refractive index number in the range from about 1.1 to about 1.4.

7. The device of claim 6, wherein the coating is polytetrafluoroethylene.

8. The device of claim 1, wherein the coating has a refractive index number of about 1.3.

9. The device of claim 1, wherein the excitation beam has a power in the range from about 1 mW to about 1000 mW.

10. The device of claim 1, wherein the excitation beam has a width in the range from about 5 $\mu$m to about 1000 $\mu$m.

11. The device of claim 1, wherein the light detector can distinguish between more than one color of fluorescent light.

12. The device of claim 1, wherein the light detector may be placed at either end or both ends of the separation capillary.

13. The device of claim 1, further comprising a plurality of capillaries.

14. The device of claim 1, wherein the buffer solution comprises a gel sieving material, a surface deactivating agent, and a buffer selected from the group consisting of tris-boric acid EDTA, potassium tartrate, and tris-acetate EDTA.

15. The device of claim 14, wherein the gel sieving material is selected from the group consisting of poly (ethylene glycol), poly(vinyl alcohol), hydroxy propyl methyl cellulose, hydroxyethylcellulose, and linear polyacrylamide.

16. The device of claim 14, wherein the surface deactivating agent is poly(vinylpyrrolidone).

17. A device for separating and detecting particles comprising:
a capillary having a first end and a second end the capillary filled with a buffer solution, the capillary having a coating that transforms the capillary into a light wave guide;
a first reservoir in fluid communication with the first end of the capillary, the first reservoir configured to contain buffer solution;
a second reservoir in fluid communication with the second end of the capillary, the second reservoir configured to contain buffer solution;
an electrical source for applying a voltage across the capillary, the voltage causing a fluorescently labeled particle positioned within the capillary to travel from a first location within the capillary to a second location within the capillary;
an excitation source for directing an excitation beam onto the capillary, such that when a fluorescently labeled particle is positioned within the capillary, the fluorescently labeled particle emits light after excitation with the excitation beam;
the excitation source capable of exciting fluorescently labeled particles at more than one position along the capillary wherein the excitation beam is rastered along part or all of the length of the capillary; and
a light detector positioned to collect fluorescent light emitted from excited fluorescently labeled particle located within the capillary, wherein the light detector comprises a fiber optic coupled end-on to the capillary.

18. The device of claim 17, wherein the coating on the capillary that transforms the capillary into a light wave guide is capable of directing the fluorescent light toward the light detector.

19. The device of claim 17, wherein the coating has a refractive index of about 1.3.

20. The device of claim 17, wherein, the coating is polytetrafluoroethylene.

21. The device of claim 17, wherein the light detector comprises low-level light detection electronics.

22. The device of claim 21, wherein the low-level light detection electronics are selected from the group consisting of photomultipliers, photodiodes, and CCD cameras.

23. The device of claim 21, wherein the light detector further comprises an optical filter, prism, grating, or light spectrometer positioned between the light detection electronics and the capillary for filtering incident light, and the resulting fluorescence.

24. The device of claim 23, wherein the optical filter comprises a high band pass filter for filtering light with a wavelength greater than about 500 nm and a notch filter.

25. The device of claim 23, wherein the optical filter comprises a narrow band pass filter which filters light other than light with a wavelength corresponding to the wavelength of the light emitted from the fluorescent label, ±10 nm.

26. The device of claim 17, wherein the excitation beam has a power in the range from about 1 mW to about 1000 mW.

27. The device of claim 17, wherein the excitation beam has a width in the range from about 5 $\mu$m to about 1000 $\mu$m.

28. The device of claim 17, wherein the light detector can distinguish between more than one color of fluorescent light.

29. The device of claim 17, further comprising a plurality capillaries.

30. The device of claim 17, wherein the buffer solution comprises a gel sieving material, a surface deactivating agent, and a buffer selected from the group consisting of tris-boric acid EDTA, potassium tartrate, and tris-acetate EDTA.

31. The device of claim 30, wherein the gel sieving material is selected from the group consisting of poly (ethylene glycol), poly(vinyl alcohol), hydroxy propyl methyl cellulose, hydroxyethylcellulose, or linear polyacrylamide.

32. The device of claim 30, wherein the surface deactivating agent is poly(vinylpyrrolidone).

33. The device of claim 30, wherein the gel sieving material is at a concentration in the range from about 0.1% to about 5% and has a viscosity in the range from about 0.5 cp to about 50 cp at room temperature.

34. The device of claim 17, wherein the capillary has a length in the range from about 5 cm to about 100 cm.

35. The device of claim 17, wherein the capillary has a length of about 20 cm.

36. A method for separation and sizing of particles in short channels by capillary electrophoresis comprising:
obtaining a sample of particles;
fluorescently labeling the particles;
loading the sample into a device for separating and sizing particles, the device comprising a capillary having a first end and a second end filled with a buffer solution, the capillary having a coating that transforms the capillary into a light wave guide, a first reservoir in fluid communication with the first end of the capillary, the first reservoir configured to contain the buffer solution, a second reservoir in fluid communication with the second end of the capillary, the second reservoir configured to contain the buffer solution, an electrical source for applying a voltage across the capillary, the voltage causing the fluorescently labeled particles to travel from a first location within the capillary to a second location within the capillary, an excitation source for directing an excitation beam onto fluorescently labeled particles within the capillary, the fluorescently labeled particles emitting fluorescent light after excitation with the excitation beam, the excitation source capable of exciting the fluorescently labeled particles at more than one position along length of the capillary, and a light detector positioned to collect the fluorescent light emitted the excited fluorescently labeled particle;

applying the voltage across the capillary;

rastering the excitation beam on the capillary;

monitoring fluorescent light in the light detector;

comparing the position of the excitation beam on the capillary when light is collected by the light detector to determine the position of the particles in the capillary; and determining the relative size of the particles from the determined position.

37. The method of claim 36, wherein the device further comprises at least one additional capillary having a first end and a second end, the at least one additional capillary filled with buffer solution and having a coating that transforms the additional capillary into a light wave guide, the at least one additional capillary being in fluid communication with the first and second reservoirs, the method further comprising obtaining a second sample of particles of a known size, fluorescently labeling the particles of the second sample, applying the voltage across the at least one additional capillary, rastering the excitation beam on the at least one additional capillary, monitoring the collection of fluorescent light in the light detector; and comparing the position of the excitation beam on the capillary when light is collected by the light detector to determine the position of the particles of known size, comparing the position of the particles of known size to the position of the sample particles to determine the size of the sample particles.

38. The method of claim 37, wherein the voltage is in the range of about 4,000 V to about 20,000 V dc.

39. The method of claim 37, wherein the capillary has a length in the range of about 5 cm to about 100 cm.

40. The method of claim 39, wherein the length is in the range of about 10 cm to about 25 cm.

41. The method of claim 39, wherein the length is about 20 cm.

42. The method of claim 37, wherein the particle is selected from the group consisting of a nucleic acid, a protein, inorganic ions, and organic ions, and neutral species.

43. The method of claim 37, wherein the coating on each of the capillaries that transforms the capillaries into a light wave guide directs the fluorescent light toward the light detector.

44. The method of claim 37, wherein the coating has a refractive index of about 1.3.

45. The method of claim 37, wherein the coating comprises polytetrafluoroethylene.

46. A method for sequencing DNA comprising:

obtaining a sample of DNA to be sequenced;

running a dideoxy sequencing reaction on the DNA sample, the sequencing reaction comprising a separate reaction mixture for each nucleotide type, each reaction mixture comprising a different flourescent label, each reaction mixture run to form a separate reaction product;

pooling the reaction products of the reaction mixtures;

loading the pooled reaction products into a device for separating and detecting particles, the device comprising a capillary having a first end and a second end filled with a buffer solution, a first reservoir in fluid communication with the first end of the capillary, the first reservoir configured to contain the buffer solution, a second reservoir in fluid communication with the second end of the capillary, the second reservoir configured to contain the buffer solution, an electrical source for applying a voltage across the capillary, the voltage causing the fluorescently labeled reaction products to travel from a first location within the capillary to a second location within the capillary, an excitation source for directing an excitation beam onto the fluorescently labeled reaction products within the capillary, the fluorescently labeled reaction products emitting fluorescent light after excitation with the excitation beam, the excitation source capable of exciting the fluorescently reaction products at more than one position along length of the capillary, and a light detector positioned to collect the fluorescent light emitted the excited fluorescently labeled reaction products;

applying the voltage across the capillary;

rastering the excitation beam on the capillary;

monitoring the collection of fluorescent light in the light detector; and comparing the position of the excitation beam on the capillary to the color of light detected by the light detector to determine the position of a corresponding nucleotide within the DNA sample.

* * * * *